United States Patent [19]

Cucinella et al.

[11] 4,296,045

[45] Oct. 20, 1981

[54] PROCESS FOR THE PREPARATION OF POLY-(-N-ALKYLIMINOALANES)

[75] Inventors: Salvatore Cucinella; Alessandro Mazzei, both of San Donato Milanese; Giovanni Dozzi, Milan, all of Italy

[73] Assignee: Snamprogetti S.p.A., Milan, Italy

[21] Appl. No.: 770,228

[22] Filed: Feb. 18, 1977

Related U.S. Application Data

[63] Continuation of Ser. No. 601,209, Aug. 1, 1975, abandoned.

[30] Foreign Application Priority Data

Aug. 2, 1974 [IT] Italy ............................ 25941 A/74
Jun. 24, 1975 [IT] Italy ............................ 24706 A/75

[51] Int. Cl.$^3$ ............................................. C07F 5/06
[52] U.S. Cl. ................................................ 260/448 R
[58] Field of Search ................................... 260/448 R

[56] References Cited

U.S. PATENT DOCUMENTS 3,651,064 3/1972 Nelson et al. ............. 260/448 R X
3,983,150 9/1976 Casensky et al. ............... 260/448 R

*Primary Examiner*—Helen M. S. Sneed
*Attorney, Agent, or Firm*—Morgan, Finnegan, Pine, Foley & Lee

[57] ABSTRACT

A poly(-N-alkyliminoalane) having the composition (HAlNR)$_n$, wherein R represents an aliphatic, cycloaliphatic, aromatic or alkyl-aromatic group, and n is a number in the range of 3 to 50, is prepared by directly reacting metallic aluminum with a primary amine having the formula H$_2$NR, wherein R has the meaning given above, in the presence of hydrogen at a pressure in the range of from 1 to 1000 kg/cm$^2$ and at least a stoichiometric quantity of aluminum, at a temperature in the range of from room temperature to the dissociation temperature of the end product, and in the presence of a promoter such as a small quantity of the poly(-N-alkyliminoalane) constituting the end product of said reaction.

10 Claims, No Drawings

PROCESS FOR THE PREPARATION OF POLY-(-N-ALKYLIMINOALANES)

This is a continuation of application Ser. No. 601,209 filed Aug. 1, 1975 now abandoned.

The present invention relates to a process for the preparation of poly(-N-alkyliminoalanes) from aluminum and primary amines which are reacted in the presence of hydrogen.

Poly(-N-alkyliminoalanes) are known compounds structurally characterized by the presence of imine unities of the type —AlH—NR— bound with one other to form [HAl—NR]$_n$ structures in which n is the association degree and R may be an aliphatic, cycloaliphatic or aromatic hydrocarbon radical.

More particularly such compounds have a oligomer or polymer character in function of the n value; whether n is equal to or lower than 10 the compounds are oligomers, as disclosed in copending applications in the name of same Applicant.

Also the uses of poly-(N-alkyliminoalanes), which we shall refer to as PIA for the sake of simplicity, are known: in fact they are used as co-catalysts active in the synthesis of polyethylene, olefine polymers and highly stereospecific diolefine polymers as well as in the reduction of organic derivatives, even with an asymmetric induction. Owing to the obtained results, such compounds are advantageously employed from an industrial point of view.

It is also known that PIA may be synthetized through various methods starting from complexes of AlH$_3$ with Lewis bases, alkali metal alanates and aluminum trisamides according to what is disclosed in "Die Makromolekulare Chemie" 122 (1969), pages 168–185, and in several patent applications in the name of the same Applicant.

All of the aforesaid methods need the expensive filtration of the reaction by products constituted by alkali metal halides and/or the employment of various solvents and, hence, the following separation processes.

Particularly, when use in made of complexes formed by aluminum hydride with Lewis bases, it is to be considered that these are obtained by reacting MAlH$_4$ (M is an alkali metal) or M'(AlH$_4$)$_2$ (M'=alkaline earth metal) with aluminum halides, particularly AlCl$_3$ and the total reaction producing PIA can be written as follows:

$$3MAlH_4 + AlCl_3 \xrightarrow{ether} 3MCl + 4 AlH_3 \quad \text{Ia}$$

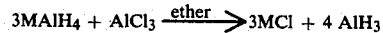

$$AlH_3 + R-NH_2 \longrightarrow 2H_2 + \frac{1}{n}(HAlNR)_n \quad \text{Ib}$$

The reaction 1a needs the presence of polar solvents, for instance ethyl ether; therefore, when hydrocarbon solutions are needed free from any trace of polar substances, as required when PIA is used as polymerization cocatalyst, it is necessary to perform, in addition to the MCl filtration, the complete removal of the polar solvent from the final reaction product and the substitution therefor of the desired solvent.

It is also true that the employment of different solvents might be avoided by using hydrocarbon solutions of AlH$_3$.NR$_3$ (obtainable by reacting MAlH$_4$ and NR$_3$.HCl). However, NR$_3$ should then be removed from the PIA hydrocarbon solution, and the removal process is an expensive one.

The methods directly employing alkali metal alanates and R—NH$_2$.HCl as starting products in the formation of PIA also need the filtration of the alkali metal halide which is formed on account of a hydride hydrogen atom as from the following scheme $$MAlH_4+HCl.H_2NR \rightarrow MCl+[AlH_3.RNH_2]+H_2$$
$$[AlH_3.RNH_2] \rightarrow 1/n[AlH-NR]_n+2H_2$$

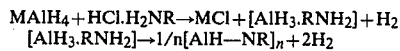

Anyhow the aforesaid methods involve the loss of hydride hydrogen. Only a certain amount of hydride hydrogen of the starting products remains in the formula PIA molecule, the other part being eliminated during the reaction as H$_2$. This renders the aforesaid processes very expensive because of the high cost of alkali (or alkaline earth) metal alanates or hydrides and/or alkali (alkaline earth) metals wherefrom alanates are obtained.

The assignee of this application owns the Italian Patent Application No. 31857 A/73 of Nov. 29, 1973 and the corresponding U.S. application, Ser. No. 524,312, filed by us on Nov. 15, 1974, relating to a simple and less expensive PIA preparation through a direct reaction of alkali or alkaline-earth metals with primary amines in the presence of only a hydrocarbon solvent.

In the case of alkali metal alanates the reaction may be schematized as follows $$MAlH_4+RNH_2 \rightarrow MH+1/n(HAlNR)_n+2H_2$$

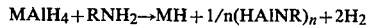

The reaction, with respect to the preceding known methods, has the following advantages:

(a) it does not involve the formation and the subsequent filtration of alkaline or alkaline-earth metal halides;

(b) therefore it does not even involve the loss of hydride hydrogen corresponding to the formation of alkali metal or alkaline-earth metal halide as from (a);

(c) it directly occurs in hydrocarbon solvent without any polar solvent, therefor the resulting PIA solution can be directly utilized as polymerization cocatalyst without any removal or recycle of polar solvents;

(d) it permits recovery of the alkali or alkaline-earth hydride, that hence may be again employed in a synthesis of MAlH$_4$ through a direct reaction of MH with aluminum and hydrogen according to known methods.

The total reaction cycle

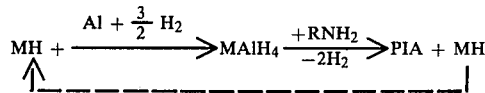

clearly emphasizes the advantage of the process according to the aforesaid application, from the economic point of view too.

Now we have found, which is the subject of the present invention, that it is possible to synthetize PIA through one single stage process which has all the aforesaid advantages and, furthermore, is more simply carried out since it does not need the previous synthesis of alanate to be reacted with amine.

Substantially the inventive process consists of the direct reaction between aluminum and a primary amine in the presence of hydrogen, according to the following scheme:

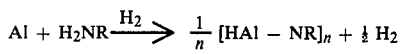

The reaction is normally carried out by starting with an aliphatic primary amine, preferably having a carbon atom number of from 1 to 20, in which the hydrocarbon chain can be either linear or branched, as well as from cycloaliphatic, aromatic, alkyl-aromatic amines, etc., together with aluminum in stoichiometric amount or in excess with respect to amine, in the presence of hydrogen.

The operations are generally carried out in the presence of a polar or merely hydrocarbon solvent, that, however, has no functional group capable of reacting with the hydride hydrogen atoms and is preferably selected from aromatic or aliphatic hydrocarbons, when PIA solutions are wished in view of particular purposes needing the total absence of polar compounds, such as, for instance, the employment as polymerization catalysts.

The reaction is carried out in the temperature range of from room temperature to the product decomposition temperature, preferably from 100° to 200° C., in the presence of hydrogen, the pressure being preferably between 50 and 300 kg/cm$^2$, for kinetic reasons.

Therefore the reaction is preferably carried out in a stainless steel autoclave with stirring. It is sufficient if the same is equipped with a screw or anchor stirrer operating at speed of 200+400 speed revolutions per minute.

In order to promote the start of the reaction, use is generally made of powdered aluminum, whose surface has been purified from possible oxide traces through a preliminary treatment according to known methods, such as, for instance, through a treatment with small amounts of metal alkyls (AlR$_3$, ZnR$_2$, etc.), metal hydrides and, particularly with small amounts of poly(N-alkyliminoalane) itself. This treatment is preferably carried out by a ball mill grinding.

The reaction run can be further increased by the presence of a suitable promoter, which has the purpose of enhancing the attack of the aluminium powder by amine. This promoter, added in amounts less than or equal to 5% by mole with respect to aluminum, is selected from alkali or alkaline-earth metals, hydride derivatives, alkyl derivatives or alanates of metals belonging to the first three groups of the periodic system. More simply the promoter may be constituted by small amounts of the reaction product itself (HAlNR)$_n$.

Furthermore use can be made also of a strong excess of aluminum that, at the end of the reaction, may be recovered or, alternatively, may be separated, in the reaction vessel, from the PIA solution and used for following reactions with amine; this fact allows the availability of more active aluminum and, hence, decreases the time necessary to complete the reaction and the other reaction conditions, i.e. temperature and/or pressure. In this case the promoter, in an amount less than or equal to 5% by mole with respect to amine, may be added only to the starting charge.

According to another embodiment of the inventive process, by using both stoichiometric aluminum and excess aluminum, it is possible to remarkably lower the reaction time and/or the other reaction conditions by feeding into the reaction vessel, together with aluminum and amine, PIA in an amount greater than the minimum one necessary for activating the reaction.

For instance it is particularly advantageous to employ PIA amounts so that the ratio 1/n(HAlNR)$_n$/RNH$_2$ ranges from 1 to 2. In the case of continuous production the PIA amount, added at the beginning, may, at the end of any preparation, be recycled for hastening subsequent reactions.

It has also been observed that the PIA preparation occurs via the formation of an intermediate, constituted by an aluminum amide derivative, which may be separated from the reaction vessel, it being characterized by a cage molecular structure having the formula (RNH—Al—NR)$_n$ in which R has the aforesaid meanings.

The separation of these products in the pure state may be effected by stopping the reaction at a N/Al ratio in solution equal to 2, or by introducing the reactants at a molar ratio amine/aluminum equal to 2.

The invention will be more clearly understood by consideration of the following examples, that however are not limitative thereof.

EXAMPLE 1

Under a nitrogen atmosphere, powdered aluminum (99.5% purity) was suspended in heptane, 2% by mole of AlEt$_3$ was added and the suspension was introduced in to a stainless steel rotating mill equipped with steel spheres and kept under stirring for 24 hours.

Then 65 ml were drawn of the suspension containing 200 mmoles of Al, that were decantated. Supernatant clear heptane (~50% of the volume) is removed and replaced by fresh heptane.

The solvent replacement operation was repeated after a two hour stirring. At the end there were added toluene up to a volume of 300 ml, 0.51 g of NaAlH$_4$ (9.4 mmoles) and 15.35 ml of anhydrous isopropylamine (mmoles 180) in that order.

The suspension was introduced into a stainless steel autoclave provided with an anchor stirrer. H$_2$ was introduced at a pressure of 135 kg/cm$^2$ and a heating was carried out, the pressure thus rising to about 200 kg/cm$^2$. The stirring was continued under these conditions for 15 hours, then the whole was slowly cooled. The autoclave was depressurized and the reaction mixture was siphon collected.

The solution filtered from residual aluminium was examined as to the atomic ratio N/Al, which was 0.98.

The solvent was then removed from the solution at reduced pressure. At the end there were obtained 15 g of white, crystalline solid as determined by the X-ray powder spectrum.

| Analysis | Al | N | H$_{active}$ |
|---|---|---|---|
| found | 29.85% | 16.35% | 11.31 meq/g |
| calculated for (HAlNC$_3$H$_7$)$_n$ | 31.71% | 16.46% | 11.75 meq/g |

Since no nitrogen is present on aluminum residue from the reaction, the yield as imine derivative may be considered quantitative.

The mass spectrometry, through the presence of ions M$^+$ at m/e 510, together with ions (M-H)$^+$ at m/e 509, (M-2H)$^+$ at m/e 508, (M-CH$_3$)$^+$ at m/e 495, emphasized the formation of HAlN-isoC$_3$H$_7$)$_6$.
In agreement:

$^1$H—NMR in benzene solution showed a doublet at τ8.49 and a sectet at τ6.29, due to the protons of the groups CH$_3$ and CH of the amine radical
the molecular weight in ethyl ether at boiling was 534 (calculated on (HAlNiso—C$_3$H$_7$)$_6$=510.48).

Furthermore the I.R. analysis showed the presence of a band νAl—H with a maximum at 1850 cm$^{-1}$ due to tetracoordinated aluminum atoms.

EXAMPLE 2

Powdered aluminum was treated with AlEt$_3$ according to example 1.

An amount of the resulting suspension corresponding to 200 mmoles of Al was decanted, then ~50% of the supernatant clear solvent was removed. Fresh heptane was added to a volume of 100 ml; a few minutes stirring was performed, a decantation was carried out, and ~50% of the solvent was removed and was replaced by fresh solvent.

This operation was repeated five times, thereafter the solution contained only traces of alkyl aluminum.

At the end to the aluminum suspension was added heptane to 300 ml, 15.35 ml of anhydrous iso-C$_3$H$_7$NH$_2$(mmoles 180) and 0.23 g of sodium (m atoms 10), in that order.

The mixture was introduced into the autoclave according to example 1. H$_2$ was fed at a pressure of 135 kg/cm$^2$ at room temperature and the whole was heated to 180° C., therefor the pressure rose to about 200 kg/cm$^2$. The stirring was continued for 15 hours under the aforesaid conditions. The autoclave was slowly cooled to room temperature and then depressurized. The reaction mixture was filtered. In the solution there was a N/Al molar ratio equal to 1.12; furthermore the chemical analysis underlined that all amine, first introduced, reacted to give the soluble polyimine derivative.

Correspondingly, on the reaction product, $^1$H—HMR in benzene showed that it was substantially hexa-(N-isopropyliminoalane), in agreement too with the results of mass spectrometry.

The pure product was obtained in the from of a crystalline solid, by cooling the reaction solution at −78° C.

| Analysis | Al | N | H$_{active}$ |
|---|---|---|---|
| found | 30.70% | 16.41% | 11.87 meq/g |
| calculated for (HAlNC$_3$H$_7$)$_6$ | 31.71% | 16.46% | 11.75 meq/g |

The molecular weight, determined by ebulliometry in ethyl ether, was 495 (calculated value for (HAlNC$_3$H$_7$)$_6$=510.48).

The I.R. spectrum in nujol showed a band νAl—H at 1850 cm$^{-1}$, in agreement with the presence of tetracoordinated aluminum.

The physical-chemical data, on which we refer to example 1, confirmed the obtaining of pure hexa (N-isopropyliminoalane).

EXAMPLE 3

To powdered aluminum (mmoles 300) was added 200 ml of toluene and 1.35 g of hexa(N-isopropyliminoalane) (mmoles 2.65).

The mixture was introduced into a mill provided with steel spheres. The stirring was continued for 20 hours.

The resulting suspension, to which was added 250 ml of toluene and 31.7 ml of iso-C$_3$H$_7$NH$_2$ (mmoles 270), was introduced into an autoclave. A pressure was applied of 135 kg/cm$^2$ at room temperature, then the temperature was raised up to 180° C., which caused the pressure to rise to about 200 kg/cm$^2$. The stirring was continued under these conditions for 16 hours, then the autoclave was slowly cooled and depressurized. The reaction mixture was recovered and filtered.

The solution was analyzed as to the atomic ratio N/Al, which was equal to 1.12. Furthermore the chemical analysis showed that all fed amine reacted to give a soluble polyimine product.

The mass spectrometry emphasized the prevailing formation of hexa(N-isopropylimine alane) near to other N-isopropylimine derivatives having a lower or higher mass, in agreement with the spectrum $1_H$ NMR.

The solution was concentrated at ml 60; 150 ml of hexane were added, and the whole was cooled at −78° C. A white, crystalline (X-ray) solid was separated, which was recovered by low temperature filtration, dried 6.3 g of product) and analyzed

| | Al | N | H$_{active}$ |
|---|---|---|---|
| found | 31.05% | 15.60% | 9.95 meq/g |
| calculated for (HAlNC$_3$H$_7$)$_n$ | 31.71% | 16.46% | 11.75 meq/g |

Mass spectrometry measurements, agreeing with $^1$H NMR measurements, showed it was substantially hexa(N-isopropyliminoalane), according to the data reported in example 1.

The I.R. spectrum in nujol showed a band Al—H al 1850 cm$^{-1}$, in agreement with tetracoordinated aluminum atoms.

EXAMPLE 4

Powdered aluminum was treated with AlEt$_3$ according to example 1. An amount of the resulting solution, corresponding to 200 mmoles, was decanted. The supernatant clear solution was removed and replaced with ml 100 of fresh toluene. A minute stirring was carried out, a decantation was performed and the supernatant liquid phase was removed.

This operation was repeated four times. At the end there were added, in this order, 17 ml of n-C$_3$H$_7$NH$_2$ (mmoles 207), 0.52 g of NaAlH$_4$ (mmoles 9.6) and toluene to a volume of 300 ml.

The suspension was introduced into an autoclave. H$_2$ was fed at a pressure of 135 km/cm$^2$ at room temperature, then the temperature was raised to 180° C. thereinafter the pressure rose to about 200 kg/cm$^2$. The stirring was continued under these conditions for 16 hours, then the remperature was slowly lowered to room temperature, the autoclave was depressurized and the reaction suspension was recovered.

The solution, filtered from the residual aluminum powder, analyzed for a N/Al atomic ratio equal to 1.04. The chemical analysis showed that fed amine reacted to give the soluble imine derivatives.

The solvent was removed under vacuum and the white residue, vacuum dried at room temperature (to give 17 g of product) was analyzed

| | Al | N | H$_{active}$ |
|---|---|---|---|
| found | 29.55% | 15.92% | 10.75 meq/g |
| calculated for | | | |

-continued

| | Al | N | $H_{active}$ |
|---|---|---|---|
| $(HAlNC_3H_3)_n$ | 31.71% | 16.46% | 11.75 meq/g |

The mass spectrometry emphasized it was substantially octa(N-n-propyliminoalane) because of the ion (M-Et)+ at m/e 651 prevailing in the spectrum. In agreement therewith the $^1$H NMR spectrum in benzene showed a triplet at $\tau 9.07$, a multiplet at $\tau 7.96$ and a triplet at $\tau 6.74$ due to the protons of the groups $CH_3$ $\beta$-$CH_2$ $\alpha$-$CH_2$ of the hydrocarbon radicals bound to the nitrogen atoms.

The I.R. spectrum in nujol showed a band $\nu$Al-H with a maximum at 1815 and 1855 cm$^{-1}$ in agreement with the presence of tetracoordinated aluminum.

EXAMPLE 5

200 mmoles of powdered aluminum, previously treated with AlEt$_3$ in heptane according to example 1 and repeatedly washed with heptane till the disappearance of aluminum in solution, were added toluene up to 300 ml, 18.8 ml of anhydrous tert-butylamine (190 mmoles), 0.5 g of NaAlH$_4$ (mmoles 9.3).

The suspension was introduced into an autoclave. A pressure was applied up to 140 kg/cm$^2$, then a heating up to 185° C. that increased the pressure up to about 205 kg/cm$^2$.

The stirring was carried out under these conditions for 16 hours, then the autoclave was slowly cooled to room temperature, depressurized and the reaction mixture was recovered. On the solution filtered from the unreacted aluminium, the mass spectrometry showed the formation of tetra(N-tert-butyl-iminoalane) [(M-CH$_3$)+ at m/e 381] near to other aluminum imine derivatives [(M-CH$_3$)+ at m/e 501, 456, 430, etc.].

It is possible to separate the different products by crystallizing at low temperature. From the reaction solution toluene was completely removed by vacuum evaporation and substituted with 170 ml of hexane.

The resulting solution was cooled at $-78°$ C. so as to isolate the less soluble reaction by-products which were removed by filtration.

The residual solution was concentrated at 50% by volume and again cooled at $-78°$ C. The precipitated crystalline white solid, vacuum dried at room temperature (to give g 3.9 of product) was constituted by tetra(N-tert-butyliminoalane).

| Analysis | Al | N | $H_{active}$ |
|---|---|---|---|
| found | 27.01% | 15.10% | 9.71 meq/g |
| calculated for $(HAlNC_4H_9)_n$ | 27.22% | 14.13% | 10.09 meq/g |

The mass spectrometry showed an ion (M-CH$_3$)+ at m/e 381. The $^1$H NMR spectrum in benzene showed a single signal as to the protons of the groups CH$_3$ at $\tau 8.56$.

The molecular weight, in boiling ethyl ether, was 376 (calculated value for $(HAlNC_4H_9)_n = 396.44$).

The I.R. spectrum in nujol showed a band $\nu$Al-H at 1850 cm$^{-1}$, in agreement with the presence of tetracoordinated aluminum.

EXAMPLE 6

To 200 mmoles of powdered Al, previously treated with AlEt$_3$ in toluene according to example 1, separated from toluene by decantation repeatedly washed with fresh toluene till the disappearance of Al in solution, were added toluene to 300 ml, 17.8 ml (175 mmoles) of sec-butylamine, 0.54 g of NaAlH$_4$ (mmoles 10).

The suspension was introduced into the autoclave. H$_2$ was fed up to a pressure of 125 kg/cm$^2$ and a heating was performed to 170° C., which increased the pressure to about 180 kg/cm$^2$.

The whole was stirred under these conditions for 15 hours, then the autoclave was cooled to room temperature, depressurized and the reaction mixture was recovered. The solution was separated through a filtration of unreacted aluminum, and evaporated under reduced pressure. A solid residue (g 17) was obtained, that was analyzed:

| | Al | N | $H_{active}$ |
|---|---|---|---|
| found | 27.41% | 14.00% | 10.25 meq/g |
| calculated for $(HalNC_4H_9)_n$ | 27.22% | 14.13% | 10.09 meq/g |

The physical-chemical determinations proved the compound to be hexa(N-sec-butyliminoalane). In fact the mass spectrum comprises ions (M-Et)+ at m/e 565. In agreement the $^1$H NMR spectrum in benzene showed a multiplet at $\tau 6.54$ (CH bound to nitrogen atom), another multiplet at $\tau 8.06$ (CH$_2$), a doublet at $\tau 8.40$ (CH$_3$ in $\beta$ position with respect to nitrogen) and a triplet at $\tau 9.04$ (CH$_3$ in $\gamma$ position with respect to nitrogen). The relative intensity of those signals was 1:2:3:3 respectively.

EXAMPLE 7

Under a nitrogen atmosphere, powdered aluminum (99.5% purity) was suspended in toluene, to which was added 2% by mole of AlEt$_3$ and the suspension was introduced into a stainless steel rotating mill containing steel spheres and kept under stirring for 24 hours. 50 ml of the suspension were drawn containing 230 mmoles of Al, that were decanted. The supernatant clear solvent was removed and replaced by fresh toluene. The solvent replacement operation was five times repeated, thereafter aluminum was completely absent from the solution. At the end, to the aluminum was added 300 ml of toluene, hexa(N-isopropyliminoalane) corresponding to 200 g atoms of aluminium.

The suspension was introduced into 1 l stainless steel autoclave, followed by a solution of 17 ml (200 mmoles) of isopropylamine in 100 ml of toluene. Hydrogen was fed at a pressure of 135 kg/cm$^2$ and a heating was carried out up to 180° C. which increased the pressure to 190 kg/cm$^2$. The stirring was carried out under these conditions for 1.5 hours; the autoclave was cooled and depressurized. The reaction mixture was filtered and the solution was analyzed as to the content of Al and N that resulted Al=0.98 g atoms/liter
N=1.01 g atoms/liter Therefrom the N/Al ratio was equal to 1.03. This corresponded to the quantitative conversion of introduced amine in hexa-(N-isopropyliminoalane) through a reaction with an aluminum equimolecular amount. For the sake of confirmation the solution was suspended and the solid residue was examined. No variation was observed on the composition and the physycal-chemical of this solid with respect to the ones of hexa-(N-isopropyluminoalane) firstly added to aluminium:

|  | Al | N | $H_{active}$ |
|---|---|---|---|
| found | 30.71% | 16.35% | 11.29 meq/g |
| calculated for $(HAlNC_3H_7)_n$ | 31.71% | 16.46% | 11.75 meq/g |

The physical-chemical measurements (mass spectrometry, $^1H$ NMR, RX) confirmed the formation of hexa-(N-isopropyliminoalane) according to the results emphasized in preceding specifications.

EXAMPLE 8

To 230 mmoles of powdered aluminum, previously treated with $AlEt_3$ in toluene according to the conditions of example 1 and, after the toluene removal, repeatedly washed with ethyl ether till the disappearance of aluminum in solution, were added, after one another, ethyl ether up to 300 ml, 17 ml of isopropylamine (200 mmoles), 0.5 g of $NaAlH_4$(mmoles 9.3). The suspension was introduced into an autoclave. $H_2$ was fed at a pressure of 135 kg/cm$^2$, the autoclave was heated to 90°–95° C., the pressure thus increasing up to 170 kg/cm$^2$. The stirring was carried out under these conditions for 1 hour, then the autoclave was cooled and depressurized. The reaction mixture was recovered and filtered. The solution was evaporated under reduced pressure, thereafter a white residue (g 16.5) was obtained, that was analyzed

|  | Al | N | $H_{active}$ |
|---|---|---|---|
| found | 31.05% | 15.71% | 12.22 meq/g |
| calculated for $(HAlNC_3H_7)_n$ | 31.71% | 16.46% | 11.75 meq/g |

The mass spectrometry, $^1H$ NMR, X-ray diffraction measurements confirmed hexa-(N-isopropyliminoalane).

Also a test was carried out in diethylether by employing the same amounts of solvent and amine, under the same conditions, but a larger excess of aluminum, whose amount was 38 g (1.4 mmoles). After 1 hour reaction the solution of hexa(N-isopropyliminoalane) was siphon recovered, after decantation, and aluminum, still in the autoclave, after a previous suspension in 300 ml of $Et_2O$, was employed in six subsequent reactions with 200 mmoles of iso-$C_3H_7NH_2$; all the reactions produced solutions of hexa-(N-isopropyliminoalane) at quantitative yield in a time lower than 1 hour.

EXAMPLE 9

The reaction between aluminum and isopropylamine was carried out as described in example 1, but the amount of hexa-(isopropylaminoalane) introduced at the beginning with the aluminum suspension, that was limited at 10 g atoms of aluminum.

After 1.5 hours reaction, the solution filtered from unreacted aluminium analyzed as follows
Al=0.275 g atoms/liter
N=0.51 g atoms/liter
corresponding to a N/Al ratio equal to 1.85. That meant the formation of hexa-(N-isopropyliminoalane) was not quantitative and the reaction mixture was constituted by hexa-(N-isopropyliminoalane) and a novel aluminum amine compound
(RNH—Al—NR)$_4$
(R=iso $C_3H_7$)
characterized by a cage structure.

This is to be considered an intermediate in the reaction between aluminum and isopropylamine to give hexa-(N-isopropyliminoalane).

It reacted with unstable $AlH_3$ or with the more stable complexes formed by $AlH_3$ with Lewis bases to give hexa-(N-isopropyliminoalane).

It was obtained in high purity if the reaction between Al and amine was stopped at a solution N/Al ratio equal to 2. In this case the product could be further and easily purified by crystallization. A typical composition was the following one

|  | Al | N |
|---|---|---|
| found | 19.31% | 20.01% |
| calculated for $(C_3H_7NH—Al—NC_3H_7)_4$ | 18.97% | 19.70% |

In agreement with the proposed tetramer structure, the mass spectrometry showed ions at m/e 568, 509, 452, 395 and 338, while the $^1H$ NMR in benzene solution showed two doublets at $\tau 8.52$ and $\tau 8.67$, having the same intensity, due to the protons $CH_3$ of the alkyl radicals on nitrogen atoms set in different molecular positions, and an envelop of two sectets set at $\tau 6.55$.

What we claim is:

1. In a process of preparing a poly-(-N-alkyliminoalane) having the composition $(HAlNR)_n$, wherein R represents a member of the group consisting of aliphatic, cycloaliphatic, aromatic and alkylaromatic radicals, and n is a number in the range of 3 to 50, the process comprising reacting metallic aluminum with a primary amine having the formula $H_2NR$, wherein R has the significance given above, in the presence of hydrogen at a pressure in the range of from 1 to 1000 kg/cm$^2$ and at least a stoichiometric quantity of said aluminum with respect to the amine, at a temperature in the range of from room temperature to the dissociation temperature of the end product, and in the presence of an initiator composition, the improvement which comprises said initiator composition being present in an amount less than about 5 mole percent with respect to said amine, said initiator composition being selected from the group of initiators consisting of alkaline or earth-alkaline metals and hydrides of aluminum and alkaline or earth-alkaline metals, poly-(-N-alkyliminoalanes) and alkyl aluminum derivatives.

2. A process as defined in claim 1, wherein said primary amine is a primary aliphatic amine whose alkyl radical contains 1 to 20 carbon atoms.

3. A process as defined in claim 1, wherein said metallic aluminum is present in the reaction mixture in an amount which is in excess of the stoichiometric quantity thereof with respect to the amine.

4. A process as defined in claim 1, wherein said initiator composition consists essentially of one of said initiators.

5. A process as defined in claim 1, wherein said initiator composition consists essentially of poly-(-N-alkyliminoalane).

6. A process as defined in claim 1, wherein said temperature is in the range of from 100° to 200° C.

7. A process as defined in claim 1, wherein said hydrogen pressure is in the range of from 50 to 30 kg/cm$^2$.

8. A process as defined in claim 1, wherein the reaction is carried out in the presence of a solvent selected from the group consisting of polar solvents and aromatic and aliphatic hydrocarbons devoid of any functional group adapted to react with hydride hydrogen atoms.

9. A process as defined in claim 1, wherein the reaction is carried out in the presence of a polar solvent.

10. A process as defined in claim 9, wherein said polar solvent comprises ethyl ether.

* * * * *